(12) United States Patent
Xu et al.

(10) Patent No.: US 11,098,999 B2
(45) Date of Patent: Aug. 24, 2021

(54) CASCADE FOURIER DOMAIN OPTICAL COHERENCE TOMOGRAPHY

(71) Applicant: University of Rochester, Rochester, NY (US)

(72) Inventors: Di Xu, Beijing (CN); Jannick Rolland-Thompson, Seneca Falls, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 16/220,321

(22) Filed: Dec. 14, 2018

(65) Prior Publication Data

US 2019/0195615 A1    Jun. 27, 2019

Related U.S. Application Data

(60) Provisional application No. 62/609,886, filed on Dec. 22, 2017.

(51) Int. Cl.
*G01B 9/02* (2006.01)
*A61B 5/00* (2006.01)

(52) U.S. Cl.
CPC ........ *G01B 9/02091* (2013.01); *A61B 5/0066* (2013.01); *G01B 9/02015* (2013.01); *G01B 9/02043* (2013.01); *A61B 5/0073* (2013.01)

(58) Field of Classification Search
CPC .............. G01B 9/0209; G01B 9/02091; G01B 9/02015; G01B 9/02027; G01B 9/02043; G01B 11/2441; A61B 5/0066; A61B 5/0073; G01M 11/005; G01M 11/0271
See application file for complete search history.

(56) References Cited

U.S. PATENT DOCUMENTS

| | | | | |
|---|---|---|---|---|
| 5,260,761 A * | 11/1993 | Barker | ............... | G01B 11/2441 356/4.1 |
| 2006/0055939 A1* | 3/2006 | Akiba | ............... | G01B 9/02014 356/497 |
| 2013/0194542 A1* | 8/2013 | Aoki | ................... | G01N 21/4795 351/206 |
| 2014/0125992 A1* | 5/2014 | Ota | .................... | G01B 9/02091 356/497 |
| 2016/0040977 A1* | 2/2016 | An | ......................... | A61B 3/102 356/479 |
| 2017/0120337 A1* | 5/2017 | Kanko | .................. | B29C 64/386 |
| 2018/0035894 A1* | 2/2018 | Yamanari | ........... | G01B 9/02041 |

OTHER PUBLICATIONS

J. Huang et al., "Maximum-likelihood estimation in Optical Coherence Tomography in the context of the tear film dynamics", Biomedical Optics Express, vol. 4, No. 10, pp. 1806-1816, Oct. 2013, DOI:10.1364/BOE.4.001806.

* cited by examiner

*Primary Examiner* — Tarifur R Chowdhury
*Assistant Examiner* — Jonathon Cook
(74) *Attorney, Agent, or Firm* — Thomas B. Ryan; Andrew J. Anderson, Esq.; Harter Secrest & Emery LLP

(57) ABSTRACT

A cascaded interferometric system for Fourier domain optical coherence tomography (OCT) in which the output of one sub-system interferometer is directed through a second sub-system interferometer for performing the Fourier transform in hardware.

21 Claims, 3 Drawing Sheets

CASCADE FOURIER DOMAIN OPTICAL COHERENCE TOMOGRAPHY

STATEMENT REGARDING FEDERALLY SPONSORED RESEARCH OR DEVELOPMENT

This invention was made with Government Support under IIP-1338877 and IIP-1822049 awarded by National Science Foundation. The government has certain rights in the invention.

TECHNICAL FIELD

The invention relates to optical metrology, including Fourier domain optical coherence tomography, particularly for freeform optical components.

BACKGROUND

Recent advances in deterministic grinding and polishing of optical quality surfaces have enabled the manufacturing of optical components with increasingly more complex surface shapes. Rotationally variant, i.e. freeform, optical components are of increasing interest to the optical design community as they allow for substantial advances in optical performance and/or packaging footprint and form factor compared to conventional systems.

A survey of recent optical designs employing freeform optical surfaces shows that freeform sag departure from best fit sphere (defined as the base sphere that minimizes the RMS sag departure) may range from <100 μm (mild) to 600 μm or more (extreme). This scale of sag departure is generally far outside the typical dynamic range of interferometry for conventional, rotationally invariant optical surfaces. Moreover, tolerance on the optical surface figure often calls for error less $\lambda/2$ to $\lambda/4$ peak-to-valley (PV) (316 nm to 158 nm at the 633 nm He—Ne wavelength typical for interferometry, respectively). The metrology instrument should be capable of measurements with uncertainty at least an order of magnitude better than the specified tolerance. Furthermore, as optical surfaces are ground and polished to tens of nanometer RMS roughness or better, non-contact measurement techniques are typically preferred if not required especially in later stages of fabrication.

A need exists for an instrument capable of non-contact, nanometer class measurements for both reflective and transmissive freeform optical components while remaining versatile across different freeform shapes.

SUMMARY

This disclosure includes instrumentation and methodologies that contribute to meeting this challenge. A cascade architecture is presented in which two interferometry systems are arranged in series. A first interferometer is arranged for Fourier domain optical coherence tomography (OCT) scanning using a broadband source and a second interferometer splits the returning signal to perform a Fourier transform in hardware by progressively varying the relative optical path lengths of the split signals and recording the resulting interference patterns of the subsequently recombined signals.

According to aspects described herein, a cascade Fourier domain OCT interferometer system includes cascaded first and second sub-system interferometers. The first sub-system interferometer can be arranged for scanning a sample against a reference surface with a broadband source beam for generating a first level output beam based on interference between a portion of the source beam returning from the sample and another portion of the source beam returning from the reference surface. The second sub-system interferometer can be arranged to split the first level output beam from the first sub-system interferometer into two further beam portions and to vary relative optical path lengths of the two further beam portions over time before recombining the two further beam portions into a second level output beam that is directed to a detector. A processor can be arranged for converting detected values of the second level output beam associated with variations in relative optical path lengths of the two further beam portions into a measurement of the sample.

The cascaded interferometer arrangement allows for non-contact measurements with nanometer class uncertainty on surfaces with sag departures at the millimeter level and slope variations in the tens of degrees range. Direct depth profile acquisition is possible in which systematic errors are readily de-coupled and the resulting signal after processing and calibration can be arranged to more closely correspond to the part under test.

A Fourier transform of the OCT signal can be performed in hardware, thus removing the need to linearize the signal with respect to wavenumber and perform Fourier transforms in software that are typical of conventional Fourier domain OCT systems, leading to reduced data processing time. Simultaneous de-coupled dual-surface measurements are possible for transmissive freeform optical components, as well as measurements of sub-surface features such as material inhomogeneity.

Embodiments also provide for measurements with interchangeable non-flat reference surfaces, for example spheres or toroidal substrates that may be used for mass-production of freeform optical components, or freeform substrates themselves to create quasi-null or null-testing configurations. Simultaneous measurements of fiducial markers allow for rapid registration of the part under test to its nominal design. Both rough and smooth optical surfaces can be measured, allowing for measurements of test parts in various stages of optics manufacturing for in process feedback.

A wide measurable spatial frequency range is possible covering figure to mid-spatial frequencies. Typical size optical parts (<φ2") can be measured without moving either the probe optics or the test part. Larger part sizes can be accommodated via mechanical actuation of the test part and/or the optical probe with a trade-off in measurement speed and uncertainty.

BRIEF DESCRIPTION OF THE DRAWING FIGURES

DETAILED DESCRIPTION

Figure 1:
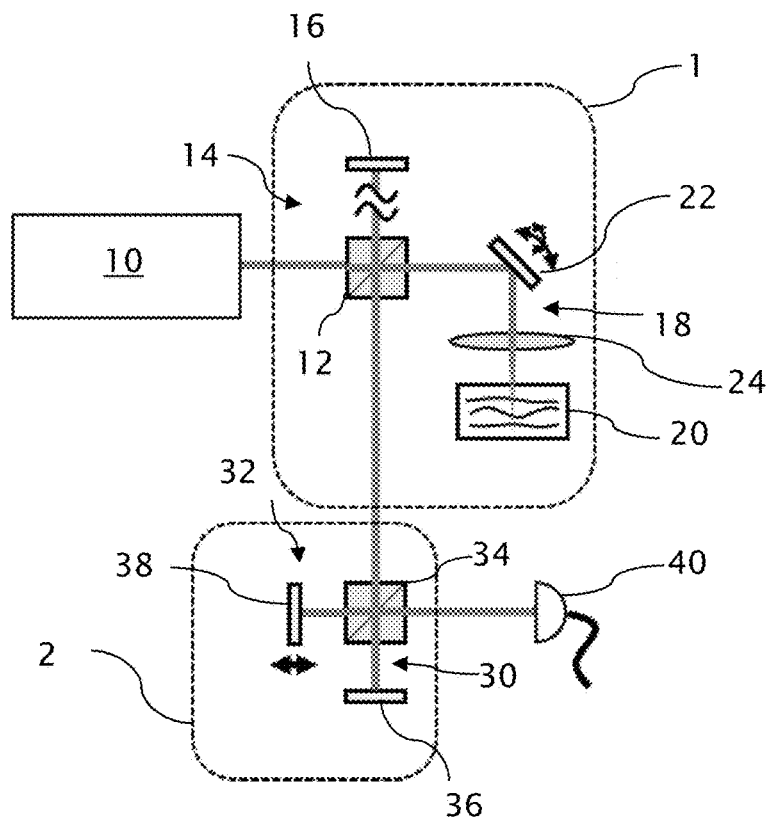
FIG. 1 is a schematic depiction of a cascaded Fourier domain OCT system in which the output of one sub-system interferometer is directed through a second sub-system interferometer in series.

A representative schematic of a cascade architecture as herein contemplated is shown in FIG. 1, where a sub-system interferometer 2 is arranged in series with a sub-system interferometer 1.

A light beam from a (laser) broadband source 10 is directed into the sub-system interferometer 1, and a beamsplitter 12 splits the light beam between a reference arm 14 that directs a resulting reference beam to and from a reference surface 16 and a sample arm 18 that directs resulting sample beam to and from a sample 20, such as a test part. Along the sample arm 18, a two-dimensional beam steering mechanism 22 together with an objective lens 24 steers the sample beam laterally across the sample 20. Additional relative motion between the sample beam and the sample can be provided by mechanical actuation involving movement of one or both of the beam optics and sample. The reference surface 16 can be placed adjacent to the surface of the sample 20 to achieve a common-path configuration, in which case the reference surface 16 can be flat, spherical, or of other known complex shapes including freeform surface shapes. After recombining the returning reference and sample beams at the beamsplitter 12 of the sub-system interferometer 2, a recombined first level output beam of the subsystem interferometer 1 is directed into the sub-system interferometer 2.

The sub-system interferometer 2 also contains two arms 30 and 32, where an optical path difference (OPD) between the two (first and second) arms 30 and 32 is scanned through time. A beamsplitter 34 splits the output beam of the subsystem interferometer 1 into a first beam portion that propagates along the first arm 30 to and from a first reflector 36 and a second beam portion that propagates along the second arm 32 to and from a second reflector 38, which is axially translatable through time. The beamsplitter 34 can take a variety of forms such as but not limited to cube, plate, or pellicle beamsplitters. The first and second beam portions are recombined at the beamsplitter 34 into a second level output beam that is directed to a detector 40 for monitoring intensity variations in the second level output beam associated with the translation of the second reflector 38 through time.

The broadband source 10 is chosen to achieve a desired coherence gating of the sample 20 through depth by limiting the temporal coherence length of the output beam. For purposes of signal detection, the detector 40 can be arranged as a photodetector with a subsequent digitizer with amplifiers and other signal processing components where necessary. Beam shaping (via e.g. spatial filter(s), beam expander(s), etc.) and spectral shaping (via e.g. bandpass filter(s), short/long pass filter(s), grating(s), etc.) can be implemented where necessary.

Figure 2:
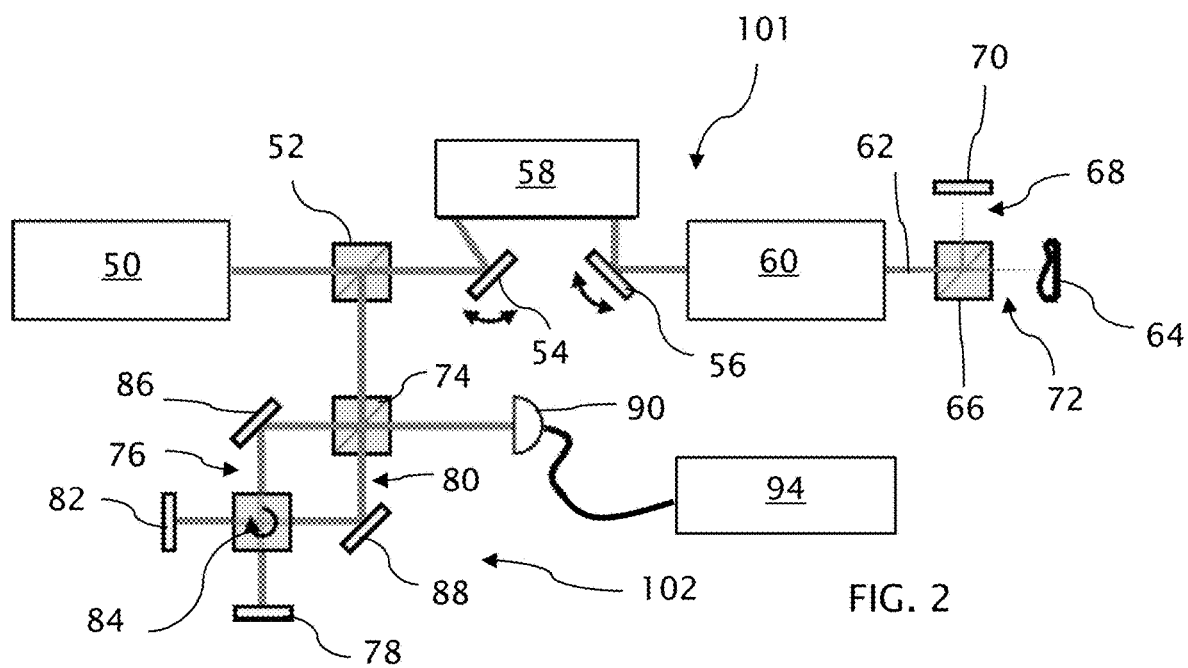
FIG. 2 is a schematic depiction of another cascaded Fourier domain OCT system in more detail.

A more detailed cascade architecture is shown in FIG. 2. A light beam of a (laser) broadband source 50 is sent through a beamsplitter 52 into a first sub-system interferometer 101, shown here in a lateral scanning configuration controlled by two orthogonally related scanning mirrors 54 and 56 separated by a pupil relay 58 for imaging one scanning mirror onto the other. The two scanning mirrors 54 and 56 can be but are not limited to galvanometer mirrors for covering a large range of scan angles and should be located at an entrance pupil of a telecentric objective lens 60 for converting the range of angular scan angles into laterally displaced beams that converge through a focus about central rays in parallel with an optical axis 62 of the telecentric objective lens 60. The scanning mirrors 54 and 56 can be controlled to trace a two-dimensional grid of focus positions over a sample 64, such as a freeform optic.

A beamsplitter 66 in the path of the converging beams splits the converging beams into a reference beam that is directed along a reference arm 68 to and from a reference surface 70 and a sample beam that is directed along a sample arm 72 to and from the sample 64. Locating the beamsplitter 66 downstream of the telecentric objective lens 60 preserves a common path for the reference and sample beams through most of the optics of the first sub-system interferometer 101. The back-reflected/back-scattered light from the reference surface 70 and the sample 64 recombines at the beamsplitter 66 and propagates back through the scanning mirrors 54 and 56 and the pupil relay 58 between them to the beamsplitter 52, where the recombined reference and sample beams are further directed to a second sub-system interferometer 102 as a first level output beam.

Although the reference surface 70 is depicted as a flat surface, higher measurement sensitivity can be achieved by using a reference surface that more closely resembles the sample 64 under test. For example, the reference surface 70 could be a sphere, or a more complex surface such as a toroidal or a known freeform component to create a quasi-null or null configuration. The toroidal component is motivated by an emerging mass-production manufacturing process involves the replication of freeform departure on top of toroidal substrates, leveraging the fact that many freeform surfaces have significant Zernike or related astigmatism in their shapes. In such case, the reference surface could be shaped as a toroidal substrate corresponding to the freeform under test. Fiducial markers can be incorporated into the reference surface, allowing for higher sensitivity as well as close integration with the manufacturing process.

A beamsplitter 74 within the second sub-system interferometer 102 splits the first level output beam from the first subsystem interferometer 101 into a first beam portion that propagates along a first arm 76 to and from a first reflector 78 and a second beam portion that propagates along the second arm 80 to and from a second reflector 82. Both beam portions pass through a rotating optical cube 84. A fold mirror 86 along the first arm 76 and a fold mirror 88 along the second arm 80 relatively orient the first and second beam portions orthogonal to the rotating optical cube 84. Rotation of the optical cube 84 progressively varies the OPD between the first and second arms 76 and 80. The cube rotation results in a variation in OPD, which is a combination of different path lengths for each arm 76 and 80 into the glass of the cube together with varying distances from the cube surfaces to the mirrors 78, 82, 86, and 88 as the cube rotates. The returning first and second beam portions are recombined at the beamsplitter 74 into a second level output beam that is directed to a detector 90 for monitoring intensity variations in the second level output beam associated with the rotation of the optical cube 84 through time.

Data Processing for Tomography Extraction

Figure 3:
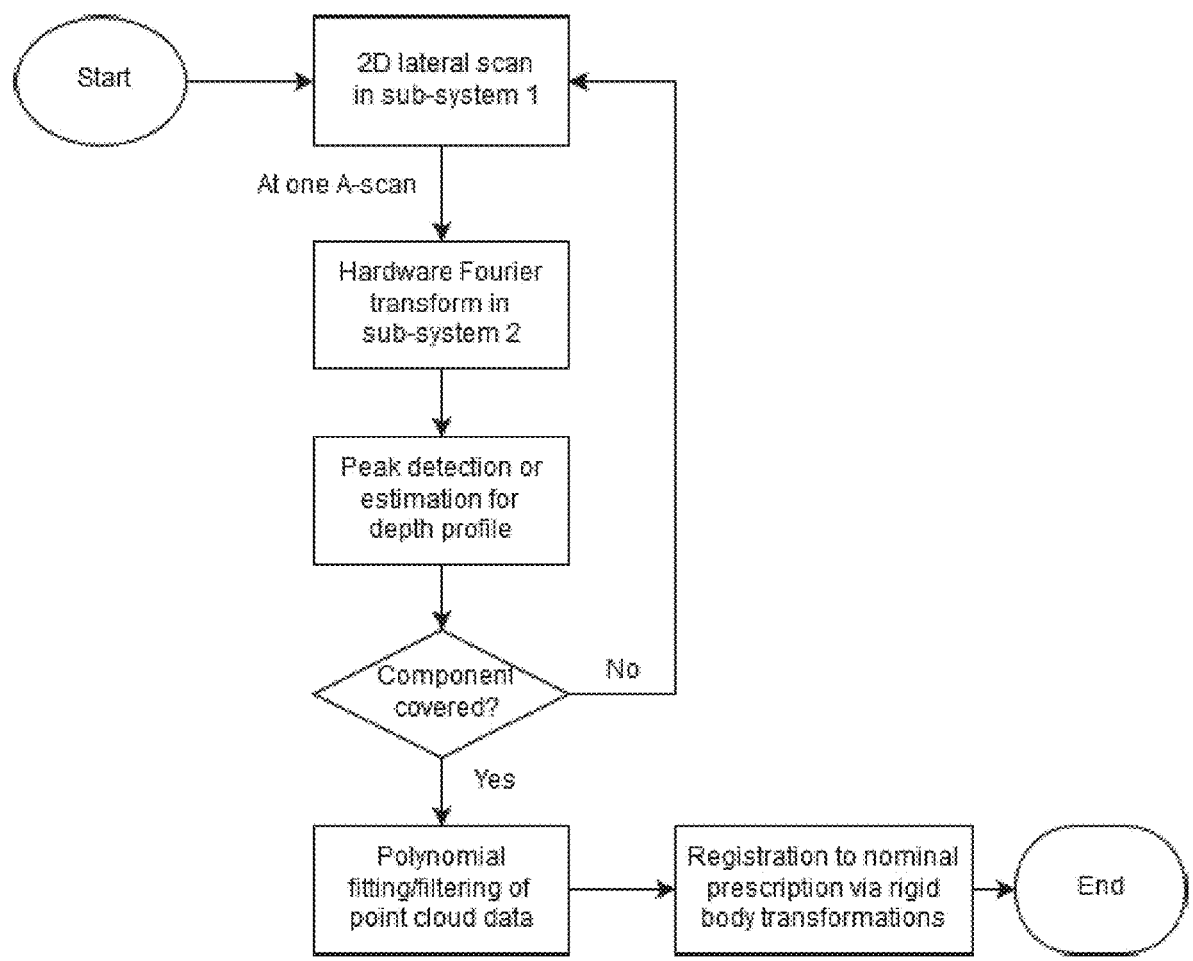
FIG. 3 is a flow chart of a tomographic imaging process for the cascaded Fourier domain OCT systems.
Figure 4:
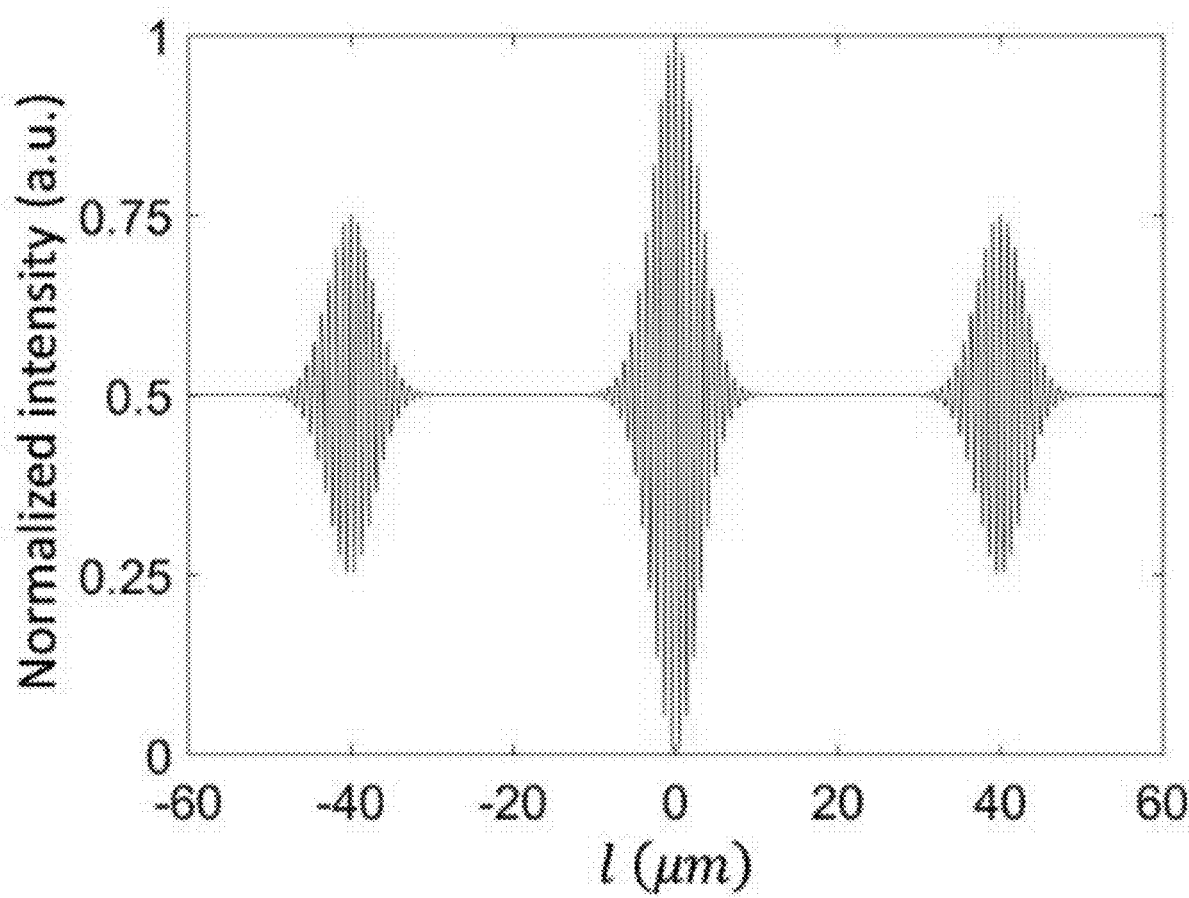
FIG. 4 is a graph plotting normalized intensities over a range of positive and negative distances representing the output signal of the second sub-system interferometer collected over a range of optical path length differences between beam portions propagating through the second sub-system interferometer.

A flowchart of a process performed by a processor 94 connected to the detector 90 for one measurement instance under this invention is summarized in FIG. 3. The processor 94 can also be used to both monitor and control the broadband source 50, the two scanning mirrors 54 and 56, the rotating optical cube 84, and well as other desired components of the two interferometers 101 and 102. Multiple measurements can be taken to assess uncertainty.

Unlike conventional Fourier domain OCT systems, the wavenumber linearization and Fourier transform are both performed in hardware. Envelope peak detection can then be performed in software to rapidly recover a depth profile for the sample. Alternatively, additional Fourier processing and advanced estimation algorithms can be performed such as a maximum likelihood estimator to lower measurement uncertainty. One such technique is described in a paper by J. Huang, E. Clarkson, M. Kupinski, K. Lee, K. L. Maki, D. S. Ross, J. V. Aquavella, and J. P. Rolland entitled "Maximum-likelihood estimation in Optical Coherence Tomography in the context of the tear film dynamics," Biomed. Opt. Express 4, 1806 (2013), the disclosure of which is hereby incorporated by reference in its entirety.

A recovered depth profile from each A-scan across a two-dimensional lateral scanning grid forms a 3D point cloud representation of the sample under test. The surface topography measurement can be registered to the nominal sag departure via rigid body transformations to assess residual error. The presence of fiducial markers enables rapid registration with minimal ambiguity. The topography measurement can also be assessed via polynomial fitting and filtering to isolate the sample surface from known noise sources and to compare the topography measurement to a nominal surface prescription. The surface mathematical prescriptions that can be used may include but are not limited to XY polynomials, phi-polynomials such as the standard and fringe Zernike polynomials and the 2D Q-polynomials, radial basis functions (RBFs), and nonuniform rational basis spline (NURBS).

Mathematical Framework of the Cascade Architecture

Let the field emitted from the laser source be denoted as $E(k)$. In the first sub-system interferometer 101, for a single surface sample, assuming reflectivity from both the reference surface 70 and the surface of the sample 64 are unity, the field emerging from the first sub-system interferometer 101 $E(k)_p$ can be written as:

$$E(k)_P = (1 + e^{i \cdot k \cdot 2z}) E(k) \quad (1)$$

where z is the sag departure of the sample surface from the reference surface with the factor of 2 to account for double-pass.

In the second sub-system interferometer 102, assuming reflectivity from both reflectors 78 and 82 are unity, the field incident on the detector $E(k,l)_D$ can be written as:

$$E(k,l)_D = (1 + e^{i \cdot k \cdot l}) E(k)_P \quad (2)$$

where l is the OPD introduced in the second sub-system interferometer 102.

The photodetector detects the intensity of the field summed over all incident wavenumbers as:

$$I(l) = \int |E(k,l)_D|^2 dk \quad (3)$$

Therefore, Eqs. (1) and (2) can substituted into Eq. (3) to obtain $$I(l) = 4\int S(k)dk + 4\int S(k)(\cos 2kz + \cos kl)dk + 2\int S(k)[\cos k(l+2z) + \cos k(l-2z)]dk \quad (4)$$

where $S(k) = |E(k)|^2$ is the power spectral density (spectrum) of the laser broadband source 50. Using the same procedure, this framework can be readily extended to non-unity, non-identical reflectivities and multi-layer sample structures.

As apparent from Eq. (4), the detected signal has three parts: 1) a constant term; 2) a modulated spectrum centered at l=0; and 3) two modulated spectra centered at l=±2z. Therefore, the peaks of the envelopes of the two displaced spectra directly yield the sample sag measurement. Additional digital signal processing algorithms can be implemented to demodulate the signal within each of the three envelopes to enhance peak detection. This routine can be performed for each point in the lateral scan to produce the final point cloud measurement of the sample under test.

Validation of Cascade Architecture in Software Simulation

A simulation was carried out in MATLAB® to represent this algorithm. As an example, a Gaussian input laser spectrum was generated and subsequently modulated by a sample sag departure of z=20 μm. This modulated spectrum was sent into the second sub-system interferometer 102 and OPD scan was performed representing optical cube 74 rotation. With a simulated signal from the first sub-system interferometer 101 measuring a point on the sample 64 that has a 20 μm sag departure, the peaks of the envelopes of the two displaced spectra produced by the second sub-system interferometer 102 are centered at ±40 μm (i.e., ±2z). The simulated detected signal is shown in FIG. 3 and is in agreement with the analytic expression.

The cascade Fourier domain OCT architecture as described above enables simultaneous ultra-broad bandwidth and ultra-fine spectral resolution with relatively low cost and compact implementation as well as linear fast Fourier transform algorithm in hardware, making it exceptionally well-suited for the task of optical metrology. A further advantage of this approach is its inherent capability to perform simultaneous measurement of fiducial markers that may be outside of the clear aperture of the sample, on top of the sample surface, or beneath the sample surface for transmissive parts. Due to the rotational variant nature of freeform optical components, registering the measurand to the nominal design is needed to assess any residual error on the part. Such fiducial markers also enable rapid orientation of the part from manufacturing to testing to assembly.

Compared to other forms of OCT, the approach described above, including the use of wide spectral bandwidths, can provide higher sensitivity and a larger dynamic range in terms of the sag and slope of the sample surface. A wide range of laser sources can be used provided the spectral bandwidth of the source meets the desired metrology requirements. The cascaded second sub-system interferometer performs a Fourier transform in hardware during data acquisition that is inherently linear in wavenumber, which can significantly reduce processing time. The three-dimensional point cloud imaging made possible by the cascade architecture and data acquisition processing enables extraction of surface topology as well as subsurface features for transmissive samples.

The telecentric scanning configuration in the first sub-system interferometer 102 avoids the need to actuate the sample and/or the lens itself, thus removing the requirement to have a priori knowledge of the part under test. This configuration also enables this invention to scan faster across the sample, mitigating for vibrational and other environmentally induced noise artifacts. While a particular scanning system may be limited to maximum measurable sample size as determined by the scanning field of the view of the objective lens, additional lateral mechanical actuation of the beam system or sample can be used to expand the range of measurement.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

The invention claimed is:

1. A cascade Fourier domain optical coherent tomography interferometer system comprising:

a first sub-system interferometer arranged for scanning a sample relative to a reference surface with a broadband source beam for generating a first level output beam based on interference between a portion of the source beam returning from the sample and another portion of the source beam returning from the reference surface;

a second sub-system interferometer that splits the first level output beam from the first sub-system interferometer into two further beam portions and progressively varies an optical path length difference between the two further beam portions over time before recombining the two further beam portions into a second level output beam that is directed to a detector; and a processor arranged for converting detected values of the second level output beam associated with the variations in the optical path length difference between the two further beam portions into a measurement of the sample.

2. The interferometer system of claim 1 in which a scanning system combined with a telecentric objective lens provide for scanning the sample relative to the reference surface.

3. The interferometer system of claim 2 in which a first beamsplitter located between the telecentric objective lens and the sample divides the source beam into a reference beam that travels to and from the reference surface and a sample beam that travels to and from the sample.

4. The interferometer system of claim 3 in which the reference beam from the reference surface and the sample beam from the sample are recombined at the first beamsplitter, and a second beamsplitter located between the broadband source for the source beam and the scanning system redirects the recombined reference and sample beams to the second sub-system interferometer as the first level output beam.

5. The interferometer system of claim 1 in which the first sub-system interferometer includes a first beamsplitter that divides the source beam into a reference beam that travels to and from the reference surface and a sample beam that travels to and from the sample.

6. The interferometer system of claim 5 in which the second sub-system interferometer includes a second beamsplitter that splits the first level output beam from the first sub-system interferometer into the two further beam portions with a first of the two further beam portions being reflected from a first reflector and a second of the two further beam portions being reflected from a second reflector.

7. The interferometer system of claim 6 in which an actuator provides for relatively adjusting optical path lengths of the first and second beam portions through a distance that is at least as long as an optical path length difference between the reference and sample beams of the first sub-system interferometer.

8. The interferometer system of claim 7 in which the actuator provides for moving at least one of the first and second reflectors.

9. The interferometer system of claim 7 in which the actuator provides for controlling an optic that varies an optical path length difference between the first and second beam portions by simultaneously changing the optical path lengths of the first and second beam portions.

10. The interferometer system of claim 9 in which the optic is an optical cube and the actuator provides for rotating the optical cube relative to at least one of the first and second beam portions.

11. The interferometer system of claim 7 in which the second beamsplitter recombines the first and second beam portions into the second level output beam that is directed to the detector.

12. A method of measuring a sample with a cascade Fourier domain optical coherent tomography interferometer system comprising steps of:

scanning a sample relative to a reference surface with a broadband source beam with a first sub-system interferometer;

generating a first level output beam based on interference between a portion of the source beam returning from the sample and another portion of the source beam returning from the reference surface;

splitting the first level output beam from the first sub-system interferometer with a second sub-system interferometer into two further beam portions;

progressively varying an optical path length difference between the two further beam portions over time with the second sub-system interferometer before recombining the two further beam portions into a second level output beam that is directed to a detector; and converting detected values of the second level output beam associated with the variations in the optical path length difference between the two further beam portions into a measurement of the sample.

13. The method of claim 12 in which the step of scanning includes combining a scanning system with a telecentric objective lens to provide for scanning the sample relative to the reference surface.

14. The method of claim 13 in which the step of generating includes dividing the source beam with a first beamsplitter located between the telecentric objective lens and the sample into a reference beam that travels to and from the reference surface and a sample beam that travels to and from the sample.

15. The method of claim 14 in which step of generating includes recombining the reference beam from the reference surface and the sample beam from the sample at the first beamsplitter and redirecting the recombined reference and sample beams with a second beamsplitter located between the broadband source for the source beam and the scanning system to the second sub-system interferometer as the first level output beam.

16. The method of claim 12 in which the step of generating includes dividing the source beam into a reference beam that travels to and from the reference surface and a sample beam that travels to and from the sample.

17. The method of claim 16 in which the step of splitting includes splitting the first level output beam from the first sub-system interferometer into the two further beam portions with a first of the two further beam portions being reflected from a first reflector and a second of the two further beam portions being reflected from a second reflector.

18. The method of claim 17 in which the step of varying includes relatively adjusting optical path lengths of the first and second beam portions through a distance that is at least as long as an optical path length difference between the reference and sample beams of the first sub-system interferometer.

19. The method of claim 18 in which the step of relatively adjusting includes moving at least one of the first and second reflectors.

20. The method of claim 18 in which the step of relatively adjusting includes varying an optical path length difference between the first and second beam portions by simultaneously changing the optical path lengths of the first and second beam portions.

21. The method of claim 18 in which the step of relatively adjusting includes rotating an optical cube relative to at least one of the first and second beam portions.

\* \* \* \* \*